United States Patent [19]
Updyke et al.

[11] Patent Number: 6,059,948
[45] Date of Patent: *May 9, 2000

[54] SYSTEM FOR PH-NEUTRAL STABLE ELECTROPHORESIS GEL

[75] Inventors: Timothy V. Updyke, Temecula; Sheldon C. Engelhorn, Cardiff-by-the-Sea, both of Calif.

[73] Assignee: Novex, San Diego, Calif.

[*] Notice: This patent is subject to a terminal disclaimer.

[21] Appl. No.: 09/229,388

[22] Filed: Jan. 11, 1999

Related U.S. Application Data

[63] Continuation of application No. 08/730,678, Oct. 11, 1996, Pat. No. 5,922,185, which is a continuation-in-part of application No. 08/221,939, Mar. 31, 1994, Pat. No. 5,578,180.

[51] Int. Cl.$^7$ .................................................. G01N 27/26
[52] U.S. Cl. ............................................ 204/468; 204/606
[58] Field of Search ..................................... 204/468–470, 204/606

[56] References Cited

U.S. PATENT DOCUMENTS

| | | | |
|---|---|---|---|
| 3,870,812 | 3/1975 | Hayes, Jr. et al. | 426/350 |
| 3,948,743 | 4/1976 | Monthony et al. | 204/180 |
| 4,139,440 | 2/1979 | Chrambach et al. | 204/180 |
| 4,209,373 | 6/1980 | Bluestein et al. | 204/180 |
| 4,481,094 | 11/1984 | de Castro et al. | 204/180 |
| 4,504,641 | 3/1985 | Nochumson | 526/238.2 |
| 4,542,200 | 9/1985 | Nochumson | 526/238.2 |
| 4,699,705 | 10/1987 | Ogawa et al. | 204/299 |
| 4,950,708 | 8/1990 | Hoshstrasser | 524/728 |
| 5,275,708 | 1/1994 | Akins et al. | 204/182.8 |
| 5,370,777 | 12/1994 | Guttman et al. | 204/182.8 |
| 5,464,516 | 11/1995 | Takeda et al.d | 204/182.9 |
| 5,578,180 | 11/1996 | Engelhorn et al. | 204/468 |

FOREIGN PATENT DOCUMENTS

| | | |
|---|---|---|
| 0 087 995 A1 | 2/1983 | European Pat. Off. . |
| 0 087 995 B1 | 2/1983 | European Pat. Off. . |
| 0 566 784 A1 | 10/1993 | European Pat. Off. . |
| 94/23092 | 10/1994 | WIPO . |

OTHER PUBLICATIONS

Chrambach et al. ("Experimental validation of the predicted properties of a multiphasic buffer system applied to polyacrylamide gel electrophoresis", Separ. Sci. (1972), 7(6), 725–45), Month unknown.
Samuel Raymond, et al., "Acrylamide Gel as a Supporting Medium for Zone Electrophorsis," *Science*, vol. 130, pp. 711–712, (1959). Month unknown.
Andrew C. Peacock, et al., "Molecular Weight Estimation and Separation of Ribonucleic Acid by Electrophoresis in Agarose–Acrylamide Composite Gels," *Biochemistry*, vol. 7, No. 2, pp. 668–674, (1968). Month unknown.
Thomas M. Jovin, "Multiphasic Zone Electrophoresis. I, II & III Steady–State Moving–Boundary Systems Formed by Different Electrolyte Combinations," *Biochemistry*, vol. 12, No. 5, pp. 871–898, (1973). Month unknown.
Thomas M. Jovin, "Multiphasic Zone Electrophoresis. IV. Design and Analysis of Discontinuous Buffer Systems with a Digital Computer," *Annals New York Academy of Science, Jovin: Computer Design of Buffer Systems*, pp. 477–496, (1973). Month unknown.
R. Ruechel, et al., Hoppe–Seyler's Z. Physiol. Chem., 356(3), pp. 1283–1288 (abstract), (1975). Month unknown.
Leslie C. Lane, "A Simple Method for Stabilizing Protein–Sulfhydryl Groups during SDS–Gel Electrophoresis," *Analytical Biochemistry*, vol. 86, pp. 655–664, (1978). Month unknown.
Andreas Chrambach, et al., "Selected buffer systems for moving boundary electrophoresis on gels at various pH values, presented in a simplified manner," *Electrophoresis*, vol. 4, pp. 190–204, (1983). Month unknown.
Michael W. Hunkapiller, et al., "Isolation of Microgram Quantitiies of Proteins from Polyacrylamide Gels for Amino Acid Sequence Analysis," *Methods in Enzymology*, vol. 91, pp. 227–232, (1983). Month unknown.
Jack Kyte, et al., "A Discontinuous Electrophoretic System for Separating Peptides on Polyacrylamide Gels," *Academic Press, Inc.*, pp. 515–522, (1983). Month unknown.
Anthony T. Andrews, "Electrophoresis, Theory, Techniques, and Biochemical and Clinical Applications", *Oxford Science Publications*, Second Edition, pp. 79–92, (1986).
A.T. Andrews, Electrophoresis, Oxford Univ. Press, pp. 20 & 126, (1986).
Malcolm Moos, Jr., et al., "Reproducible High Yield Sequencing of Proteins Electrophoretically Separated and Transferred to an Inert Support," *The Journal of Biological Chemistry*, vol. 263, No. 13, pp. 6005–6008, (1988). Month unknown.
Kenneth G. Christy, Jr., et al., "Modifications for SDS–Page of Proteins", *BioTechniques*, vol. 7, No. 7, pp. 692–693, (1989). Month unknown.
Jeffery, D. Fritz, et al., "Factors Affecting Polyacrylamide Gel Electrophoresis and Electroblotting of High–Molecular–Weight Myofibrillar Proteins," *Analytical Biochemistry*, vol. 180, pp. 205–210, (1989). Month unknown.
K. Nakamura et al., Electrophoresis, pp. 10, 29–33, (1989).
B.D. Hames, et al., "Gel Electrophoresis of Proteins, A Practical Approach," *The IRL Press at Oxford University Press*, Second Edition, pp. 1–50, (1990). Month unknown.
Jens Wiltfang, et al., "A new multiphasic buffer system for sodium dodecly sulfate–polyacrylamide gell electrophoresis of proteins and peptides with molecular masses 100 000–1000, and their detection with picomolar sensitivity," *Electrophoresis*, vol. 12, pp. 352–366, (1991). Month unknown.
"Migration Tables" and "Buffer Selection Guide," NOVEX Brochure, (1991). Month unknown.

(List continued on next page.)

*Primary Examiner*—Jill Warden
*Assistant Examiner*—Alex Noguerola
*Attorney, Agent, or Firm*—Fish & Neave; James Trosino

[57] ABSTRACT

A gel and buffer system for gel electrophoresis wherein separation occurs at neutral pH.

14 Claims, No Drawings

OTHER PUBLICATIONS

Wayne F. Patton, et al., "Tris–Tricine and Tris–Borate Buffer Systems Provide Better Estimates of Human Mesothelial Cell Intermediate Filament Protein Molecular Weights than the Standard Tris–Glycine System," *Analytical Biochemistry*, vol. 197, pp. 25–33 (Aug. 15, 1991).

"Electrophoresis, The NOVEX System: The Fast, Easy Way To Your Answer!," NOVEX Brochure (1992). Month unknown.

Martin de Llano, et al., "Increased electrophoretic mobility of sodium sulfite–treated jack bean urease," *Electrophoresis*, vol. 13, pp. 300–304, (1992). Month unknown.

Harold Swerdlow, et al., "Stability of capillary gels for automated sequencing of DNA," *Electrophoresis*, vol. 13, pp. 475–483, (1992). Month unknown.

"Technically Speaking . . . , NOVEX Pre–mixed Buffers, Fast, Easy, Reproducible Electrophoresis Buffers," NOVEX Brochure (1993). Month unknown.

Suraj P. Bhat, "DNA Sequencing on Minigels: An Alternative Technique for routine Analysis," *Academic Press, Inc.*, pp. 560–562, (1993). Month unknown.

Harold Swerdlow, et al., "Reloading and Stability of Polyacrylamide Slab Gels for Automated DNA Sequencing," *BioTechniques*, vol. 16, No. 4, pp. 684–693, (1994). Month unknown.

Piero Carninci, et al., "A discontinuous buffer system increasing resolution and reproducibility in DNA sequencing on high voltage horizontal ultrathin–layer electrophoresis," *Electrophoresis*, vol. 16, pp. 1836–1845, (1995). Month unknown.

Robert C. Allen, et al., "Discontinuous electrophoresis revisited: A review of the process," *Applied and Theoretical Electrophoresis*, vol. 6, pp. 1–9, (1996). Month unknown.

"The Protein Society," Protein Science Program & Abstracts, vol. 5, Suppl. 1 (1996). Month unknown.

David Lide, editor, CRC Handbook of Chemistry & Physics, 77th edition, pp. 7–12, (1996–97). Month unknown.

SYSTEM FOR PH-NEUTRAL STABLE ELECTROPHORESIS GEL

This application is a continuation of application Ser. No. 08/730,678, filed Oct. 11, 1996 now U.S. Pat. No. 5,922,185, which is a continuation-in-part of application Ser. No. 08/221,939, filed Mar. 31, 1994, now U.S. Pat. No. 5,578,180, the disclosure of which is incorporated by reference herein in its entirety.

This invention relates to techniques for gel electrophoresis. More particularly this invention relates to a novel system for gel electrophoresis at approximately neutral pH.

BACKGROUND OF THE INVENTION

Gel electrophoresis is a common procedure for the separation of biological molecules, such as deoxyribonucleic acid (DNA), ribonucleic acid (RNA), polypeptides and proteins. In gel electrophoresis, the molecules are separated into bands according to the rate at which an imposed electric field causes them to migrate through a filtering gel.

The basic apparatus used in this technique consists of a gel enclosed in a glass tube or sandwiched as a slab between glass or plastic plates. The gel has an open molecular network structure, defining pores which are saturated with an electrically conductive buffered solution of a salt. These pores through the gel are large enough to admit passage of the migrating macromolecules.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known mobility, the mobility of other macromolecules can be determined. The size of the macromolecule can then be calculated.

The rate of migration of macromolecules through the gel depends upon three principle factors: the porosity of the gel; the size and shape of the macromolecule; and the charge density of the macromolecule. It is critical to an effective electrophoresis system that these three factors be precisely controlled and reproducible from gel to gel and from sample to sample. However, maintaining uniformity between gels is difficult because each of these factors is sensitive to many variables in the chemistry of the gel system.

Polyacrylamide gels are commonly used for electrophoresis. Polyacrylamide gel electrophoresis or PAGE is popular because the gels are optically transparent, electrically neutral and can be made with a range of pore sizes. The porosity of a polyacrylamide gel is in part defined by the total percentage of acrylamide monomer plus crosslinker monomer ("% T") it contains. The greater the concentration, the less space there is between strands of the polyacrylamide matrix and hence the smaller the pores through the gel. An 8% polyacrylamide gel has larger pores than a 12% polyacrylamide gel. An 8% polyacrylamide gel consequently permits faster migration of macromolecules with a given shape, size and charge density. When smaller macromolecules are to be separated, it is generally preferable to use a gel with a smaller pore size such as a 20% gel. Conversely for separation of larger macromolecules, a gel with a larger pore size is often used, such as an 8% gel.

Pore size is also dependent upon the amount of crosslinker used to polymerize the gel. At any given total monomer concentration, the minimum pore size for a polyacrylamide gel is obtained when the ratio of total monomer to crosslinker is about 20:1, (the usual expression for this ratio would be "5% C").

Several factors may cause undesirable variation in the pore size of gels. Pore size can be increased by incomplete gel polymerization during manufacture. Hydrolysis of the polyacrylamide after polymerization can create fixed negative charges and break down the crosslinks in the gel, which will degrade the separation and increase the pore size. An ideal gel system should have a reproducible pore size and no fixed charge (or at least a constant amount) and should be resistant to change in chemical characteristics or the pore size due to hydrolysis.

The size of the macromolecule varies between different macromolecules; the smaller and more compact the macromolecule the easier it will be for the macromolecule to move through the pores of a given gel. Given a constant charge density, the rate of migration of a macromolecule is inversely proportional to the logarithm of its size.

For accurate and reproducible electrophoresis, a given type of macromolecule should preferably take on a single form in the gel. One difficulty with maintaining uniformity of the shape of proteins during gel electrophoresis is that disulfide bonds can be formed by oxidation of pairs of cysteine amino acids. Different oxidized forms of the protein then have different shapes and, therefore, migrate through the gel run with slightly different mobilities (usually faster than a completely reduced protein, since the maximum stokes radius and minimum mobility should occur with a completely unfolded form). A heterogeneous mixture of forms leads to apparent band broadening. In order to prevent the formation of disulfide bonds, a reducing agent such as dithiothreitol (DTT) is usually added to the samples to be run. The shape of DNA and RNA macromolecules is dependent on temperature. In order to permit electrophoresis on temperature-dependent DNA and RNA molecules in their desired form, separations are done at a controlled temperature.

The charge density of the migrating molecule is the third factor affecting its rate of migration through the gel—the higher the charge density, the more force will be imposed by the electric field upon the macromolecule and the faster the migration rate subject to the limits of size and shape. In SDS PAGE electrophoresis, the charge density of the macromolecules is controlled by adding sodium dodecyl sulfate (SDS) to the system. SDS molecules associate with the macromolecules and impart a uniform charge density to them, substantially negating the effects of any innate molecular charge. Unlike proteins, the native charge density of DNA and RNA is generally constant, due to the uniform occurrence of phosphate groups. Thus, charge density is not a significant problem in electrophoresis of DNA and RNA.

SDS PAGE gels are usually poured and run at basic pH. The most common PAGE buffer system employed for the separation of proteins is that developed by Ornstein (1) and modified for use with SDS by Laemmli (2). Laemmli, U. K. (1970) *Nature* 227, 680–686. The Laemmli buffer system consists of 0.375 M tris (hydroxy methyl) amino-methane (Tris), titrated to pH 8.8. with HCl, in the separating gel. The stacking gel consists of 0.125 M Tris, titrated to pH 6.8. The anode and cathode running buffers contain 0.024 M Tris, 0.192 M glycine, 0.1% SDS. An alternative buffer system is disclosed by Schaegger and von Jagow. Schaegger, H. and von Jagow, G., *Anal. Biochem.* 1987, 166, 368–379. The stacking gel contains 0.75 M Tris, titrated to pH 8.45 with HCl. The separating gel contains 0.9 M Tris, titrated to pH 8.45 with HCl. The cathode buffer contains 0.1 M Tris, 0.1 M N-tris(hydroxymethyl)methylglycine (tricine), 0.1% SDS. The anode buffer contains 0.2 M Tris, titrated to pH 8.9 with HCl. For both of these systems Tris is the "common ion" which is present in the gel and in the anode and cathode buffers.

In the Laemmli system, the pH of the trailing phase in the stacking gel is about 8.9. In the separating gel, the trailing phase pH is about 9.7. At this pH, primary amino groups of proteins react readily with unpolymerized acrylamide, thiol groups are more subject to oxidation to disulfides, or reaction with unpolymerized polyacrylamide, than at neutral pH and acrylamide itself is subject to hydrolysis.

The shape of the DNA and RNA macromolecules is also dependent on a fourth important factor, temperature. The temperature-dependent shape of DNA and RNA is caused by the interaction of two macromolecules containing complementary sequences and the interaction of complementary sequences in a single macromolecule. Some techniques require that the DNA remain in its double-stranded form. Typically, such separations are done in Tris borate ethylene diamine tetra-acetic acid (TBE) buffer, consisting of 0.09 M Tris, 0.09 M boric acid, and 0.002 M ethylene diamine tetra-acetic acid (EDTA) on either polyacrylamide or agarose gels. In general, these separations are done at lower temperatures to maintain the double-stranded structure. In the absence of denaturants, DNA's and RNA's structure is fairly stable and not significantly affected by temperature.

In other techniques, dissociation of the two DNA strands (known as "melting") is utilized to effect the separation. Such methods require careful temperature control in order to produce a consistent separation. One method, non-isotopic single-strand conformational polymorphism ("Cold SSCP"), utilizes a dissociative sample buffer with heat to melt the strands, a TBE buffer, and a polyacrylamide gel. In Cold SSCP, temperatures of 4 to 35° C. are used to allow variable-conformation renaturation to occur between mutant strands, and temperature changes of only a few degrees can significantly alter the number of mutants seen. See Hongyo, et al., *Nucleic Acids Research,* 21, 3637 (1993). Another method, employed in DNA sequence analysis, typically utilizes TBE buffers containing 6 to 8 M urea and/or 2 to 12 M formamide, and elevated temperatures. It is important that the temperature remain high enough—typically 45 to 55° C.—to maintain fully melted DNA or RNA. Gels are usually polyacrylamide and sometimes substituted acrylamide polymers. For example, certain alkyl-substituted polyacrylamide gels are described in Shoor et al., U.S. Pat. No. 5,055,517.

These DNA and RNA separation methods are characterized by the use of continuous buffer systems, which use the same buffer species and generally, but not necessarily, in the same concentrations in the gel, the anode chamber, and the cathode chamber. These buffers usually are comprised of Tris and boric acid with EDTA added to inhibit hydrolytic enzyme activity. The TBE buffer system typically does not provide good stability when used in pre-cast gels, made and stored for periods of weeks at 4° C. The polymer tends to break down, generating a fixed charge which leads to distortion particularly at the cathode end of the gel where resolution is especially important. Urea also tends to break down under alkaline pH at 4° C. When large concentrations of urea are present, the ionic breakdown products can be present at a large enough concentration to disrupt the separation and cause loss of resolution.

Other buffer systems for DNA and RNA separations employ Tris/acetate, Tris/phosphate, and Tris/glycylglycine. While these buffer systems may be formulated near pH 7, the $pK_a$ of Tris causes them to shift to an alkaline pH during electrophoresis especially near the cathode. The applicants have found that the polyacrylamide and urea tend to break down during electrophoresis for DNA sequencing due to the high temperatures (50° C.) employed for several hour runs when Tris is used as the buffering base. This breakdown leads to higher current and lower resolution than might be obtained with a neutral pH buffer system, so that the DNA sequence read length is reduced and read errors are increased.

The need for uniformity and predictability is magnified in precast electrophoresis gels which are manufactured by an outside vendor and then shipped to the laboratory where the electrophoresis will be performed. Precast gels must control the properties discussed above and they must be able to maintain this control throughout shipping and storage. The shelf life of many precast gels is limited by the potential for hydrolysis of acrylamide and/or buffer constitution during storage at the high pH of the gel buffer.

It is a disadvantage of a high pH gel that the polyacrylamide gel is subject to degradation by hydrolysis and has a limited shelf-life.

It is a further disadvantage of a high pH gel that proteins react readily with unpolymerized acrylamide which may interfere with subsequent analysis of the protein such as peptide sequencing.

It is a still further disadvantage of a high pH gel that thiol groups are subject to oxidation to disulfides causing a decreased resolution of separated macromolecules.

It is a further disadvantage of a high pH gel that buffer constituents such as urea break down readily.

SUMMARY OF THE INVENTION

It is an object of this invention to produce a neutral gel system that reduces protein reaction with unpolymerized acrylamide thereby enhancing yield and resolution.

It is a further object of this invention to produce a neutral gel system that prevents formation of disulfides from free thiol groups thereby enhancing yield and resolution.

It is also an object of this invention to produce a neutral gel system that reduces degradation of the polyacrylamide gel by hydrolysis thereby increasing the stability of a gel during electrophoresis and the useful shelf-life of a precast gel, and better resolution.

It is also an object of this invention to produce a neutral gel system that reduces breakdown of buffer constituents, such as urea.

In accordance with this invention, applicants describe a gel and buffer system wherein separation occurs at neutral pH and proteins remain completely reduced. Applicants also describe a gel and buffer system wherein storage of the gel and subsequent electrophoresis of macromolecules (such as DNA, RNA, polypeptides and proteins) occurs at neutral pH. The above and other objects and advantages of the present invention will be apparent upon consideration of the following detailed description.

DETAILED DESCRIPTION OF THE INVENTION

Applicants describe a gel and buffer system wherein separation occurs at neutral pH and proteins remain completely reduced. Advantageously, at this neutral pH, primary amino groups of proteins react less readily with unpolymerized acrylamide because protonation of protein amino groups greatly reduces their reactivity to acrylamide or other related blocking agents. Furthermore, at this neutral pH, thiol groups are less subject to oxidation than at higher pH and polyacrylamide itself is less subject to hydrolysis.

The result is a gel system with improved stability of the gel matrix and stock solutions. Gels prepared according to this system can be stored under refrigeration for over a year without loss of performance due to acrylamide hydrolysis. Also, stock buffers without reducing agents and stock gel solutions without polymerization initiator can be stored for at least several weeks at room temperature with no loss of performance. An additional benefit is that a single gel recipe, using the same buffer for the stacking and separating gels, can be used with two different running buffers to give two separation systems. Using this feature, an 8% gel, for example, can cover a protein separation range of 2 to 200 kDa.

In one embodiment of this invention a polyacrylamide gel of between about 3% and about 25% (% T) acrylamide is polymerized using from about 1% to about 6% crosslinker (% C) using a gel buffer comprising a primary organic amine or substituted amine with a $pK_a$ near neutrality, titrated with approximately half as much HCl (on a molar basis), so that the pH of the buffer is approximately neutral. In a preferred embodiment the gel is polymerized using from about 2% to about 5% crosslinker (% C) using a gel buffer comprising bis-(2-hydroxyethyl) iminotris (hydroxymethyl) methane (Bis-Tris) titrated with HCl. Different separation characteristics can be obtained by running the gel with either a 3-(N-morpholino) propanesulfonic acid (MOPS) or 2-(N-morpholino) ethanesulfonic acid (MES), buffer. 2 mM to 10 mM thioglycolic acid (TGA) or 2 mM to 10 mM sodium bisulfite is added to the running buffer to maintain a reducing environment in the gel during electrophoresis.

Applicants also describe another gel and buffer system for separation of macromolecules (including DNA, RNA, polypeptides and proteins) wherein separation occurs at neutral pH. This gel and buffer system may be a discontinuous or continuous buffer system, but is particularly useful in a continuous system. A continuous buffer system is one using the same buffer species and generally, but not necessarily, in the same concentrations in the gel, the anode chamber and the cathode chamber. This gel and buffer system permits higher resolution during electrophoresis when alkaline-labile compounds such as polyacrylamide and urea are present. This gel and buffer system also permits higher resolution when elevated temperatures are used. Advantageously, at this neutral pH, urea is less subject to hydrolysis. Furthermore, polyacrylamide itself is less subject to hydrolysis.

This gel and buffer system also possesses improved stability of the gel matrix and stock solutions. Gels prepared according to this system can be stored under refrigeration for over a year without loss of performance due to acrylamide hydrolysis. Also, stock buffers and stock gel solutions without polymerization initiator can be stored for at least several weeks at room temperature with no loss of performance.

In an embodiment of this gel and buffer system an electrophoresis gel is uniformly saturated with a gel buffer solution comprising a primary organic amine or substituted amine with a $pK_a$ near neutrality, titrated with approximately an equimolar amount of acid or zwitterionic compound, so that the pH of the buffer is between about pH 6 and pH 8, preferably between pH 5.5 to pH 7.5, and most preferably 6.5 to 7.0. The electrophoresis gel may be any agarose or polyacrylamide gel. Preferably, the electrophoresis gel comprises between 3% and 25% (% T) acrylamide polymerized using from about 1% to about 6% cross linker (% C). More preferably, this polyacrylamide gel is polymerized using from about 2% to about 5% crosslinker (% C). Preferably, the amine comprises Bis-Tris or N-(2-hydroxyethyl) morpholine, and most preferably, Bis-Tris. Suitable acids and zwitterionic compounds are hydrochloric acid, tricine, acetic acid, piperazine-N,N'-2-ethanesulfonic acid, 3-(N-morpholino)-propanesulfonic acid, 2-(N-morpholino)-ethanesulfonic acid, N-(2-acetamido)-2-aminoethanesulfonic acid, 2-(N-morpholino)-2-hydroxypropanesulfonic acid, N-tris-(hydroxymethyl)-2-ethanesulfonic acid, N-2-hydroxyethyl-piperazine-N-2-ethanesulfonic acid, N,N-bis-(hydroxyethyl)-2-aminoethanesulfonic acid, and 3-(N-tris-(hydroxymethyl) methylamino)-2-hydroxypropanesulfonic acid. Tricine, 2-(N-morpholino)-ethanesulfonic acid, and piperazine-N, N'-2-ethanesulfonic acid are preferred for use in the buffer for a continuous gel and buffer system for separation of DNA and RNA because the resulting system has separation characteristics similar to the commonly used TBE gel systems. Tricine is most preferred for that use. Preferably, the gel buffer comprises Bis-Tris titrated with tricine.

In a gel and buffer system, current increases and migration rates decline as the performance of the gels decline. The increase in current has been attributed to alkaline-catalyzed hydrolysis of urea present at 36% to 42% concentration. Any breakdown in a neutral substance present at a large concentration, which produces a charged species will tend to disrupt the electrophoresis. This disruption arises from the extra current produced, which in turn increases joule heating without aiding the separation. In addition, a discontinuity arises from the anionic and cationic hydrolysis products forming in the gel that are not present in the cathode and anode buffers. Hydrolysis of gel buffer species or additives takes place independently from the gel matrix composition. The decrease in migration rate may be attributed to higher fixed charge in the gel caused by alkaline-catalyzed hydrolysis of the gel's polyacrylamide. The fixed charge leads to significant counter-flow of water, which can retard a macromolecule's migration rate. It has been found that problems of gel instability producing lower resolution, increased current, decreased migration rates can be solved with gels buffered near neutrality and with buffer substances having a $pK_a$ near neutrality. Such buffering systems improve the performance of fresh or pre-cast polyacrylamide gels, and fresh or pre-cast gels containing alkaline-labile materials, such as urea or formamide, even when the gels are made with base-stable polymers.

The inventors also have discovered the value of using different buffer substances in the cathode, gel, and anode buffers. A group of substitutions relating to cost and throughput have been discovered. The anionic substance used in the gel or the cathode buffer need not be present in the anode buffer since the anions do not migrate out of the anode buffer. In fact, the use of chloride or other strong acids in the anode buffer serves to increase the conductance of the buffer, thereby increasing the net voltage drop across the gel and decreasing run times. Such acids are also typically much less expensive as compared to those employed in the cathode buffer. Similarly, the base used to adjust the pH of the cathode buffer need not be the same as that used in the gel. At a neutral pH, sodium hydroxide, Tris, and other organic bases with a basic $pK_a$ have a higher conductance and often lower cost than Bis-Tris or other bases with a $pK_a$ near neutrality. Using sodium or Tris salts in the cathode buffer will also decrease the gel run times. Often, the anode and cathode buffers are used at a higher concentration than in the gel, further increasing their conductance and decreasing gel run times. Thus, using different, more conductive anode and cathode buffer species than in the gel buffer increases throughput and decreases costs.

It was also found that Tris or Bis-Tris may be used in the anode buffer with no visible effect on the separation quality. Because of its higher $pK_a$, Tris gradually infiltrates the anode end of the gel increasing that region's conductance, causing the voltage drop to fall locally. Thus, the macromolecules near the anode slow down and the separation compresses, while the macromolecules near the cathode experience a higher voltage drop increasing their migration and relative separation. This effect of Tris actually improves the resolution of macromolecules at the cathode end of the gel where it is most needed. Tris is the preferred choice for routine use, because it is available at significantly lower cost than Bis-Tris and can improve read lengths.

The preferred embodiment of this invention uses Tris chloride in the anode buffer, the sodium or Tris salt of the acid or zwitterionic compound in the cathode buffer, and Bis-Tris as the gel buffer amine. For protein and polypeptide separations, the most preferred cathode buffers are sodium or Tris salts of MOPS and MES, combined with a Bis-Tris chloride gel buffer. For DNA and RNA separations, the most preferred cathode buffers are sodium or Tris salts of tricine, combined with a Bis-Tris tricine EDTA running buffer. When the buffer chambers are small, the most preferred molar concentrations of the cathode and anode buffers are five times that present in the gel buffer. These buffer systems provide the benefits of a neutral pH gel during both storage and running, the least cost, and the fastest run times.

These and other embodiments can be understood by reference to the following illustrative and comparative examples.

EXAMPLES

Tris, Bis-Tris, MES, tricine, MOPS and Piperazine-N,N'-2-ethanesulfonic acid (PIPES) were purchased from Sigma (St. Louis, Mo.) or Research Organics (Cleveland, Ohio). Thioglycolic acid (TGA), dithiothreitol (DTT) and beta-mercaptoethanol (BME) were from Sigma. All other chemicals were reagent, "ultra pure" or "electrophoresis grade" from standard sources.

In Example 1 through 6, gels were cast in 1 mm thickness mini-gel cassettes from NOVEX (San Diego Calif.) and run in an X-Cell minicell. The Bis-Tris separating gel and stacking gels were prepared from a 30% T/2.5% C acrylamide/BIS stock solution and a 7x Bis-Tris stock solution (2.5M Bis-Tris, 1.5M HCl, pH 6.5). To prepare the separating gel, the stock solutions were blended with ultra pure water to a final concentration 8% T, 0.357M Bis-Tris, to which was added 0.2 ul/ml N,N,N',N'-tetra-methyl-ethylene-diamine (TEMED). After degassing, 2.0 ul/ml of a 10% solution of ammonium persulfate (APS) was added, the gel was immediately poured into the cassette then overlaid with water. Polymerization was allowed to proceed for at least 30 minutes at room temperature (RT), the water was removed and a 4% stacking gel applied. The stacking gel was prepared in the same fashion as the separating gel, except that the final concentration obtained was 4% T, the TEMED concentration was increased to 0.4 ul/ml and the APS solution increased to 5.0 ul/ml. MOPS running buffer consisted of 50 mM MOPS, 50 mM Bis-Tris (or Tris), 0.1% SDS, 1 mM EDTA. MES running buffer consisted of 50 mM MES, 50 mM Bis-Tris (or Tris), 0.1% SDS, 1 mM EDTA. Sample buffer (2x) consisted of 0.25 M Bis-Tris, 0.15 M HCl, 10% (w/v) Glycerol, 2% SDS, 1 mM EDTA, 0.03% Serva Blue G, and 200 mM DTT. Samples containing a set of protein standards were heated for 15 min at 70 degrees before application. Bovine serum albumin (BSA), chicken egg ovalbumin, alkylated insulin A and B chain, soybean trypsin inhibitor, and bovine erythrocyte carbonic anhydrase were included in the standard. Sample volume was 5 ul in all cases.

Example 1

The protein standards were separated on an 8% Bis-Tris/Cl gel with MOPS running buffer in the absence of a reducing agent. The resulting separation pattern was very similar to that obtained on an 8% Tris/glycine gel (Laemmli), with proteins 20,000 and smaller remaining in the stack along with the tracking dye. The BSA band was somewhat diffuse and shifted toward the anode. The Ovalbumin band was also somewhat diffuse.

Example 2

The protein standards were separated on an 8% Bis-Tris/Cl gel with MOPS running buffer in the presence of TGA in the cathode buffer. Again, the separation pattern was very similar to that obtained on an 8% Tris/glycine (Laemmli) gel, with proteins 20,000 and smaller remaining in the stack along with the tracking dye. The presence of the reducing agent, 5 mM TGA, in the cathode buffer provided for better resolution of the proteins BSA and Ovalbumin compared to the gel run without TGA.

Example 3

The protein standards were separated on an 8% Bis-Tris/Cl gel with MOPS running buffer in the presence of sodium bisulfite in the cathode buffer. Again, the separation pattern was very similar to that obtained on an 8% Tris/glycine (Laemmli) gel, with proteins 20,000 and smaller remaining in the stack along with the tracking dye. The presence of the reducing agent, 5 mM sodium bisulfite, in the cathode buffer provided for better resolution of the proteins BSA and Ovalbumin compared to the gel run without sodium bisulfite.

Example 4

The protein standards were separated on an 8% Bis-Tris/Cl gel with MES running buffer in the absence of a reducing agent. The protein separation was very similar to that obtained from an 12% Tris/tricine (Schaegger) gel. All proteins were resolved from the stack including insulin A and B chain (3500 and 2500 daltons, respectively). When the gel is run without TGA, soybean trypsin inhibitor had a more prominent doublet.

Example 5

The protein standards were separated on an 8% Bis-Tris/Cl gel with Bis-Tris/MES running buffer in the presence of TGA in the cathode buffer. Again, all proteins were resolved from the stack including insulin A and B chain (3500 and 2500 daltons, respectively). The presence of the reducing agent, 5 mM TGA, in the cathode buffer provided for better resolution of the protein soybean trypsin inhibitor. Carbonic anhydrase ran as a tight, sharp band under all conditions tested.

Example 6

The protein standards were separated on an 8% Bis-Tris/Cl gel with Bis-Tris/MES running buffer in the presence of sodium bisulfite in the cathode buffer. Again, all proteins were resolved from the stack including insulin A and B chain (3500 and 2500 daltons, respectively). The presence of the reducing agent, 5 mM sodium bisulfite, in the cathode buffer provided for better resolution of the protein soybean trypsin inhibitor. Carbonic anhydrase ran as a tight, sharp band under all conditions tested.

Although MES and MOPS were selected as desirable running buffers for protein separation because the resulting system has separation characteristics similar to the commonly used Laemmli and Schaegger gel systems, it was found that a range of buffers are suitable for use in this system. Among the additional buffers giving good results were [N-(2-acetamido)]-2-aminoethanesulfonic acid (ACES), 2-[N-morpholino]-2-hydroxypropanesulfonic acid (MOPSO), N-Tris-(hydroxymethyl)-2-ethanesulfonic acid (TES), N,N-bis-(hydroxyethyl)-2-aminoethanesulfonic acid (BES), N-2-hydroxyethyl-piperazine-N-2-ethanesulfonic acid (HEPES), and 3-(N-Tris-(hydroxymethyl)methylamino)-2-hydroxypropanesulfonic acid (TAPSO).

All the proteins that exhibit some band broadening and/or mobility shifts when run in the absence of TGA or sodium bisulfite, have in common a composition that includes multiple cysteines (BSA, for instance, has 35 cysteines). On the other hand carbonic anhydrase, which always runs cleanly, has no cysteines. Moreover, if the reduced proteins are alkylated before running, they run as sharp homogeneous bands even in the absence of a reducing agent.

Cysteine-containing proteins appear to give generally sharper bands in the Laemmli system than the neutral system, when both are run with 100 mM mercaptoethanol or DTT in the sample buffer but without TGA in the running buffer. Since thiol oxidation is more favored as the pH increases, it would be expected that the higher pH of the Laemmli system would cause oxidation of disulfide to be at least as pronounced as it is in the neutral pH system. However, DTT and similar "neutral" thiol reducing agents are weak acids (with $pK_a$'s around pH 8–9). Thus, at basic pH, these reducing agents migrate into the gel and, if present at sufficient concentration, provide some protection against oxidation of sulfhydryls. At a neutral separating pH, DTT from the sample buffer is in an uncharged form and will remain behind in the sample well. Thus, no reducing agent migrates into the gel.

To maintain proteins in a reduced form during electrophoresis at neutral pH, it was found advantageous to use a reducing agent that would migrate into the gel at neutral pH. Sodium bisulfite (2–10 mM) was found to maintain a reducing environment in the gel during electrophoresis. Fully reduced TGA (or similar negatively charged thiols) give similar results at comparable concentrations. However, partially oxidized TGA will promote partial oxidation of protein thiols. Because reduction (oxidation) of protein thiols will take place via disulfide interchange, the ratio of reduced to oxidized thiols in the protein will substantially reflect the ratio of reduced to oxidized thiols in the TGA. Conversely, sulfite oxidizes to sulfate, which does not participate in redox reactions under conditions found in the gel. Therefore, regardless of the sulfite/sulfate ratio in a partially oxidized preparation of sulfite, as long as sufficient sulfite remains, proteins will be protected against thiol oxidation.

It was also found that Tris could be substituted for Bis-Tris in the running buffer with no visible effect on the separation quality. Bis-Tris may be preferred where the protein will be intentionally modified post-separation. Bis-Tris is a tertiary amine and will not interfere with the protein modifying agents which react through primary amines. Tris, however, is the preferred choice for routine use, because it is available at significantly lower cost than Bis-Tris.

Example 7

A 14.7% T/5% C TBE urea gel was made in the following manner. To prepare the separating gel solution, a 30% acrylamide/ 1.6% bis-acrylamide stock solution (47.5 ml), and a 5× gel buffer stock solution containing 0.45 M Tris, 0.45 M boric acid, and 0.01 M EDTA, pH 8.18 (20 ml) were mixed with urea (36 g), TEMED (20 ul), and enough water was added to make 100 ml. The final solution pH was 8.87. It was degassed, a 10% ammonium persulfate solution ("10% APS") (12.8 ul) was added to 6.4 ml, and poured into a 1 mm thick mini-gel cassette from NOVEX (San Diego, Calif.). A comb-forming gel solution was made similarly, with the following differences: acrylamide/bis solution (12.7 ml), TEMED (50 ul), and no urea; to 1.0 ml of this solution was added 10% APS (0.1 Ml) and it was immediately poured on top of the separating gel solution. A 1 mm 10-well comb (NOVEX) was added, and the gels were allowed to polymerize for at least 30 minutes at room temperature. They were then run after storage in sealed pouches with 1× gel buffer containing 7M at different temperatures.

The gels were run fresh or after storage at either 4° C. or 35° C. Samples employed were a 10b Oligo DNA standard (BRL, Bethesda, Md.) or an 18-mer custom-synthesized DNA fragment (Synthetic Genetics, San Diego, Calif.). Gels were run in an X-Cell mini-cell (NOVEX) at 180 volts for 80 minutes, using 1× gel buffer in both the anode and cathode chambers. Finally, the bands were visualized by treating with Stains-All solution (Sigma) for 15 minutes then destaining in 20% methanol for 10 minutes.

Compared to fresh gels, the gels stored at 4° C. showed a gradual loss of band sharpness and an increase in current during the electrophoresis. The loss of sharpness leads to less resolution between bands. After 2 weeks at 4° C., the band width had doubled as compared to fresh gel bands. When stored at 35° C. for 1 week, the gels ran with higher current but the dye front only migrated 80% as far in 80 minutes. The gel itself retained the stain, and the bands were fuzzy and indistinct. After three weeks, no bands could be seen and the gels were very fragile.

Example 8

Gels were prepared, stored, and run as described in Example 7, except that the 5× gel buffer was composed of 0.45 M Bis-Tris, 0.45 M tricine, and 0.01 M EDTA pH 7.27, the final gel solution pH was 7.70, and the running buffer was 0.05 M Tris, 0.05 M tricine, 0.001 M EDTA. These gels showed no significant change in band sharpness, running current, or migration distances when stored for up to 3 weeks at 35° C. or for several months at 4° C.

Example 9

Gels were prepared, stored, and run as described in Example 7, except that the 5× gel buffer was composed of 0.125 M N-(2-hydroxyethyl) morpholine (HEM), 0.083 M acetic acid, and 0.002 M EDTA pH 7.0, and the final gel solution pH was 7.21. These gels showed no significant change in band sharpness, running current, or migration distances when stored for up to three weeks at 35° C. or for several months at 4° C. However, the gels turned yellow on storage at 35° C.

Example 10

Mini-DNA sequencing gels were prepared from the same separating gel solution as described in Example 7, except that only 23.3 ml of acrylamide/bis solution was employed, the urea was increased to 42 g, and the TEMED was increased to 50 ul. It was used without degassing by adding 10% APS (50 ul) to 10 ml of the solution, and pouring between 11 cm wide by 22 cm long thick glass plates with 0.25 mm spacers. The gels were allowed to polymerize for 60 minutes at room temperature, then run the same day.

Samples employed were an M-13 DNA sequencing reaction prepared with $S^{35}$-label using a USB Sequenase kit, version 2, (United States Biochemicals, Cleveland, Ohio). They were run in a custom-made DNA sequencing chamber at 15 watts (about 50° C.). Finally, the bands were visualized by autoradiography. The gels had a read length of 120 bases with a 5% error rate (95% accuracy).

Example 11

Gels were prepared and run as in Example 10, except that the 5× gel buffer was composed of 0.5 M Bis-Tris, 0.84 M tricine, and 0.01 M EDTA pH 7.2 and the final gel solution pH was 7.50. The gels had a read length of 137 bases with a 1.5% error rate (98.5% accuracy).

Example 12

The separating gel solution was prepared as in Example 7, except that a SoaneGel SQ solution (a solution of substituted acrylamide and substituted bis-acrylamide cross-linkers, available from Soane Biosciences Inc., Hayward, Calif.) was used for the polymer at 6% T, and the TEMED was increased to 88 ul. After initiation of the gel solution (40 ml) with 10% APS (200 ul), the gels were poured in plates with 0.35 mm spacers for an ABI Model 377 DNA Sequencer (Applied Biosystems Division of Perkin Elmer Corp., Foster City, Calif.), and allowed to polymerize at room temperature for 2 hours. The gels were loaded with a pGEM sequencing reaction and run with 1× TBE buffer at 30 V/cm, generating 55° C. They had a read length of 815 bases; at 550 bases the error rate was 1.5% (98.5% accuracy).

Example 13

Gels were prepared and run as in Example 12, except that the 5× gel buffer was composed of 0.5 M Bis-Tris, 0.84 M tricine, and 0.01 M EDTA pH 7.2, and the final gel solution pH was 7.5. The gels were run with 1× gel buffer at 30 V/cm, generating 55° C., and had a read length of 866 bases; at 550 bases the error rate was 1.1% (98.9% accuracy).

Although the invention has been explained in relation to its preferred embodiments, it is to be understood that various modifications thereof will become apparent to those skilled in the art. The foregoing disclosure is not intended or to be construed to limit the present invention, or to otherwise exclude any such other embodiments, adaptions, variations and equivalent arrangements, the present invention being limited only by the claims appended hereto and the equivalents thereof.

We claim:

1. A continuous buffer gel electrophoresis system comprising:
   an electrophoresis gel comprising a compound subject to base-catalyzed hydrolysis, the gel uniformly saturated with a gel buffer comprising an organic amine with a $pK_a$ near neutrality and a zwitterionic compound comprising a base that has a $pK_a$ between 6 and 9, the gel buffer having a pH between pH 5.5 and pH 7.5.

2. The system of claim 1, wherein the zwitterionic compound is selected from the group consisting of: N-tris(hydroxymethyl)methylglycine, piperazine-N,N'-2-ethanesulfonic acid, 3-(N-morpholino)-propanesulfonic acid, 2-(N-morpholino)-ethanesulfonic acid, N-(2-acetamido)-2-aminoethanesulfonic acid, 2-(N-morpholino)-2-hydroxypropanesulfonic acid, N-tris-(hydroxymethyl)-2-ethanesulfonic acid, N-2-hydroxyethyl-piperazine-N-2-ethanesulfonic acid, N,N-bis-(hydroxyethyl)-2-aminoethanesulfonic acid, and 3-(N-tris-(hydroxymethyl)methylamino)-2-hydroxypropanesulfonic acid.

3. The system of claim 1, wherein the compound is polyacrylamide.

4. The system of claim 1, wherein the compound is urea.

5. The system of claim 1, wherein the zwitterionic compound is N-tris(hydroxymethyl)methylglycine.

6. The system of claim 1, wherein the amine is Bis(2-hydroxyethyl)iminotris(hydroxymethyl)methane.

7. The system of claim 1, wherein the gel buffer comprises formamide.

8. A method for performing electrophoresis using a continuous buffer gel, the method comprising:
   providing an electrophoresis gel comprising a compound subject to base-catalyzed hydrolysis;
   uniformly saturating the gel with a gel buffer comprising an organic amine with a $pK_a$ near neutrality and a zwitterionic compound comprising a base that has a $pK_a$ between 6 and 9, the gel buffer having a pH between pH 5.5 and pH 7.5.

9. The method of claim 8, wherein the zwitterionic compound is selected from the group consisting of: N-tris(hydroxymethyl)methylglycine, piperazine-N,N'-2-ethanesulfonic acid, 3-(N-morpholino)-propanesulfonic acid, 2-(N-morpholino)-ethanesulfonic acid, N-(2-acetamido)-2-aminoethanesulfonic acid, 2-(N-morpholino)-2-hydroxypropanesulfonic acid, N-tris-(hydroxymethyl)-2-ethanesulfonic acid, N-2-hydroxyethyl-piperazine-N-2-ethanesulfonic acid, N,N-bis-(hydroxyethyl)-2-aminoethanesulfonic acid, and 3-(N-tris-(hydroxymethyl)methylamino)-2-hydroxypropanesulfonic acid.

10. The method of claim 8, wherein the compound is polyacrylamide.

11. The method of claim 8, wherein the compound is urea.

12. The method of claim 8, wherein the zwitterionic compound is N-tris(hydroxymethyl)methylglycine.

13. The method of claim 8, wherein the amine is Bis(2-hydroxyethyl)iminotris(hydroxymethyl)methane.

14. The method of claim 8, wherein the gel buffer comprises formamide.

* * * * *